US012409396B2

(12) United States Patent
Johnson et al.

(10) Patent No.: US 12,409,396 B2
(45) Date of Patent: Sep. 9, 2025

(54) SPIRAL WOUND PROTEIN SEPARATION DEVICE

(71) Applicant: W. L. GORE & ASSOCIATES, INC., Newark, DE (US)

(72) Inventors: Matthew A Johnson, Newark, DE (US); Michael C. McManaway, Newark, DE (US); Kenneth A. Zukor, Newark, DE (US); Vineet Rakesh, Newark, DE (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 1036 days.

(21) Appl. No.: 17/290,985

(22) PCT Filed: Nov. 5, 2018

(86) PCT No.: PCT/US2018/059193
§ 371 (c)(1),
(2) Date: May 3, 2021

(87) PCT Pub. No.: WO2020/096563
PCT Pub. Date: May 14, 2020

(65) Prior Publication Data
US 2022/0032209 A1  Feb. 3, 2022

(51) Int. Cl.
*B01D 15/38* (2006.01)
*B01D 15/22* (2006.01)
(Continued)

(52) U.S. Cl.
CPC ......... *B01D 15/3809* (2013.01); *B01D 15/22* (2013.01); *B01D 63/101* (2022.08);
(Continued)

(58) Field of Classification Search
CPC .... B01D 15/3809; B01D 15/22; B01D 15/38; B01D 15/3804; B01D 29/237;
(Continued)

(56) References Cited

U.S. PATENT DOCUMENTS 6,294,090 B1 * 9/2001 Nussbaumer .......... B01D 61/00
210/143
2018/0250637 A1 * 9/2018 Jons ..................... B01D 63/107

FOREIGN PATENT DOCUMENTS

WO       2017/058496 A1    4/2017
WO    WO 2017/176522 A1 * 10/2017 ............. B01D 15/22

* cited by examiner

*Primary Examiner* — Akash K Varma
(74) *Attorney, Agent, or Firm* — Faegre Drinker Biddle & Reath LLP

(57) ABSTRACT

The present invention is directed to an affinity chromatography device that has a normal flow and which separates a targeted protein from aqueous mixtures. The chromatography device includes a housing containing therein a spiral wound membrane assembly that includes at least one inner intermediate material that forms an outer flow channel, at least one polymer membrane that contains therein inorganic particles, and at least one outer intermediate material that forms an inner flow channel sequentially positioned around a central core having a solid outer wall. An aqueous mixture is passed through the outer flow channel, through the polymer membrane where the targeted protein is removed, and then through an inner flow channel. The affinity chromatography device further includes an inlet flow distributor containing an inlet and an outlet flow distributer containing an outlet. Additionally, the chromatography device has a dimensionless resistance parameter that is less than 0.08.

11 Claims, 3 Drawing Sheets

(51) Int. Cl.
  *B01D 63/10* (2006.01)
  *B01D 69/14* (2006.01)
  *B01D 71/02* (2006.01)
  *B01D 71/36* (2006.01)
  *C07K 1/22* (2006.01)
  *G01N 30/38* (2006.01)
  *G01N 30/60* (2006.01)
  *G01N 30/88* (2006.01)

(52) U.S. Cl.
  CPC ......... *B01D 63/107* (2022.08); *B01D 69/147* (2013.01); *B01D 69/148* (2013.01); *B01D 71/027* (2013.01); *B01D 71/36* (2013.01); *C07K 1/22* (2013.01); *G01N 30/38* (2013.01); *G01N 30/60* (2013.01); *G01N 30/88* (2013.01); *G01N 2030/8831* (2013.01)

(58) Field of Classification Search
  CPC .... B01D 63/107; B01D 63/101; B01D 63/10; B01D 69/147; B01D 69/148; B01D 69/14; B01D 71/027; B01D 71/36; B01D 71/02; C07K 1/22; G01N 30/38; G01N 30/60; G01N 30/88; G01N 2030/8831; B01J 20/281; B01J 20/282; B01J 20/283
  USPC ...................................................... 210/198.2
  See application file for complete search history.

SPIRAL WOUND PROTEIN SEPARATION DEVICE

FIELD

The present disclosure relates generally to affinity chromatography, and more specifically to a protein separation device that contains a spiral wound membrane assembly that has a normal flow, that enables the separation of a targeted protein from an aqueous mixture, and has dimensionless resistance parameter that is less than 0.08.

BACKGROUND

Chromatographic methods generally are used to separate and/or purify molecules of interest such as proteins, nucleic acids, and polysaccharides from a mixture. Affinity chromatography specifically involves passing the mixture over a matrix having a ligand specific (i.e. a specific binding partner) for the molecule of interest bound to it. Upon contacting the ligand, the molecule of interest is bound to the matrix and is therefore retained from the mixture. Affinity chromatography provides certain advantages over other types of chromatography. For example, affinity chromatography provides a purification method that can isolate a target protein from a mixture of the target protein and other biomolecules in a single step in high yield.

Despite the advantages of current affinity chromatography devices, there exists a need in the art for a chromatography device that can be used at shorter residence times than conventional devices while providing the same binding capacity or better binding capacities than current offerings and that is re-useable.

SUMMARY

One embodiment relates to an affinity chromatography device that includes (1) an exterior housing, (2) an inlet flow distributor that includes an inlet to permit fluid to flow into the housing, (3) a centrally located core, (4) a wound membrane assemble surrounding the core, and (5) an outlet end cap that includes an outlet to permit fluid to flow out of the housing. The wound membrane assembly includes at least one inner intermediate material forming an inner flow channel, a polymer membrane having therein inorganic particles having a nominal particle size, and at least one outer intermediate material forming an outer flow channel. The chromatography device has a dimensionless resistance parameter that is less than 0.08 and a normal flow. In some embodiments, the dimensionless resistance parameter ranges from 0.001 to 0.07. The intermediate material may be a porous fluoropolymer film, a porous non-fluoropolymer film, a porous non-woven material, a porous woven material, or a combination thereof. In at least one embodiment, the polymer membrane is a porous polytetrafluoroethylene membrane.

A second embodiment relates to an affinity chromatography device that includes (1) an exterior housing, (2) an inlet flow distributor that includes an inlet to permit fluid to flow into the housing, (3) a centrally located core, (4) a wound membrane assemble surrounding the core, (5) an inlet end cap positioned at one end of the wound membrane assembly, and (6) an outlet end cap positioned at an opposing end of the wound membrane assembly. The wound membrane assembly includes at least one inner intermediate material forming an inner flow channel, a polymer membrane having therein inorganic particles having a nominal particle size, and at least one outer intermediate material forming an outer flow channel. In some embodiments, the dimensionless resistance parameter ranges from 0.001 to 0.07. The intermediate material may be a porous fluoropolymer film, a porous non-fluoropolymer film, a porous non-woven material, a porous woven material, or a combination thereof. In at least one embodiment, the polymer membrane is a porous polytetrafluoroethylene membrane.

A third embodiment relates to a method for separating a target protein or antibody from an aqueous mixture that includes passing an aqueous mixture containing a targeted protein or antibody in a normal flow through a spirally wound membrane assembly from an outer flow channel to an inner flow channel and through a polymer membrane containing inorganic particles having a nominal particle size. The wound membrane assembly includes at least one inner intermediate material forming an inner flow channel, the polymer membrane having therein inorganic particles having a nominal particle size, and at least one outer intermediate material forming an outer flow channel. The chromatography device has a dimensionless resistance parameter that is less than 0.08. In some embodiments, the dimensionless resistance parameter ranges from 0.001 to 0.07.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting. It is to be understood that, as used herein, the term "on" is meant to denote an element, such as a polymer membrane, is directly on another element or intervening elements may also be present. It is to be appreciated that the terms "spiral wound membrane assembly" and "membrane assembly" may be used interchangeably herein. In addition, the "spiral wound membrane assembly" and "membrane assembly" as used herein is meant to include both the polymer membrane alone and the polymer membrane with the intermediate non-woven material.

The present invention is directed to an affinity chromatography device that separates a targeted protein from aqueous mixtures and that has a dimensionless resistance parameter that is less than 0.08. The chromatography device includes a housing containing therein a spiral wound membrane assembly that includes at least one polymer membrane that contains therein inorganic particles. The polymer membrane may be wound around a central core. An affinity ligand may be bonded to the inorganic particles and/or to the polymer membrane. The membrane assembly separates an outer flow channel from an inner flow channel. In addition, the chromatography device has a dimensionless resistance parameter that is less than 0.08.

Figure 1:
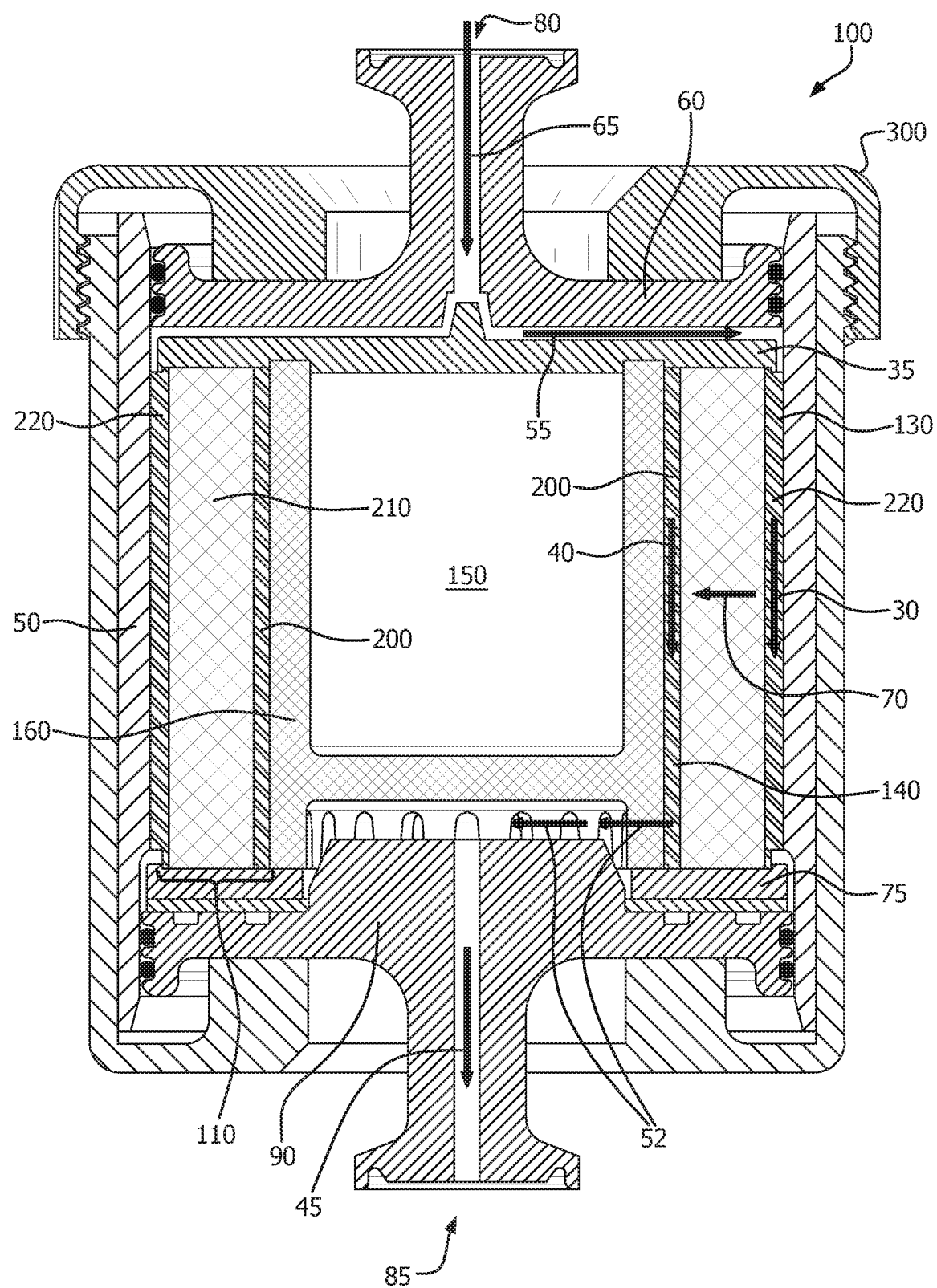
FIG. 1 is a schematic cross-section of spiral wound, normal flow chromatography device that flows an aqueous mixture from an outer flow channel to an inner flow channel in accordance with at least one embodiment.

Looking at FIG. 1, an exemplary spiral wound chromatography device 100 is depicted. In forming the chromatography device 100, at least one polymer membrane containing therein inorganic particles is wrapped around a cylindrical core 150 to form a spiral wound membrane assembly 110. In some embodiments, at least one inner intermediate material 200 may be circumferentially positioned against (e.g., wound around) the core 150 to a desired width or a pre-designated amount. The polymer membrane containing inorganic particles therein 210 is then wound around the core 150 over the inner intermediate material 200 to a desired width or a pre-designated amount, and an outer layer of at least one outer intermediate material 220 is circumferentially positioned on (e.g., wound around) the polymer material 210 a desired width or a pre-designated amount to form a membrane assembly 110. The cylindrical core 150 may have a hollow or solid interior. In either instance, the core 150 contains a solid outer wall 160 so that an aqueous mixture flowing through the chromatography device 100 flows within the inner flow channel 140 (formed of the inner intermediate material(s)), which is discussed in detail below. The use of a hollow core 150 reduces the amount of material used to form the core 150, reduces the weight of the device 100, and reduces manufacturing costs.

The membrane assembly 110 and central core 150 may be positioned within a flow path housing 50. In exemplary embodiments, the flow path housing 50 is cylindrical. In the embodiment depicted in FIG. 1, the outer intermediate material(s) 220 forms the outer flow channel 130 and the inner intermediate material(s) 200 form the inner flow channel 140. It is to be appreciated that the intermediate material(s) 200, 220 in the embodiments described herein may be different or they may be the same. Additionally, two or more intermediate materials may be used to form one or both of the outer flow channel 130 and the inner flow channel 140. In use, an aqueous mixture flows into the inlet 80 positioned within the inlet flow distributor 60 in the direction of arrow 65 where it is directed towards the outer flow channel 130 via the inlet flow distributor 60 and/or the inlet endcap 35. The inlet flow distributor 60 and/or the inlet endcap 35 directs the aqueous mixture 90 degrees from the feed direction towards the outer flow channel 130. This redirection promotes a more uniform flow of the aqueous mixture into the outer flow channel 130. The outer flow channel 130 is located between the flow path housing 50 and the wound polymer membrane 210. The flow distributors 60, 90 may be a polyolefin or coated with a polyolefin.

The aqueous mixture flows through the outer flow channel 130 (i.e., outer intermediate material(s) 220) in the direction of arrow 30 and across the wound polymer membrane 210 in a normal direction (e.g., a normal flow) as shown by arrow 70. As the aqueous mixture is passed in a normal flow from the outer flow channel 130 and across the wound polymer membrane 210, the affinity ligand reversibly binds to the targeted protein, thereby effectively removing it from the aqueous mixture. The protein-free aqueous mixture then enters the inner flow channel 140 (i.e., inner intermediate material(s) 200) located between the solid outer wall 160 of the central core 150 and the wound polymer membrane 210. The protein-free aqueous mixture flows through the inner flow channel 140 in direction of arrow 40.

The protein-free aqueous mixture then is redirected at the bottom of the inner flow channel 140 by an outlet end cap 75 and/or an outlet flow distributor 90 towards the central portion of the chromatography device 100 as depicted by arrows 52. The protein-free aqueous mixture then flows out of the chromatography device 100 through outlet 85 located within the outlet flow distributor 90 in the direction of arrow 45. The flow path housing 50 may be positioned within a pressure containment housing 300. The pressure containment housing 300 may be formed of an organic, inorganic or metallic material, so long as the flow distributors 60, 90 and pressure containment housing 300 does not hinder the operation of the chromatography device. It is to be appreciated that the diameter and/or height of the central core 150 (and/or the width and/or height of the membrane) can be adjusted to achieve a much larger volume without negatively impacting performance of the device. Additionally, the targeted protein may be removed from the affinity ligand, for example, by passing a fluid that has a lower pH through the device, as is known by those of skill in the art.

Figure 2:
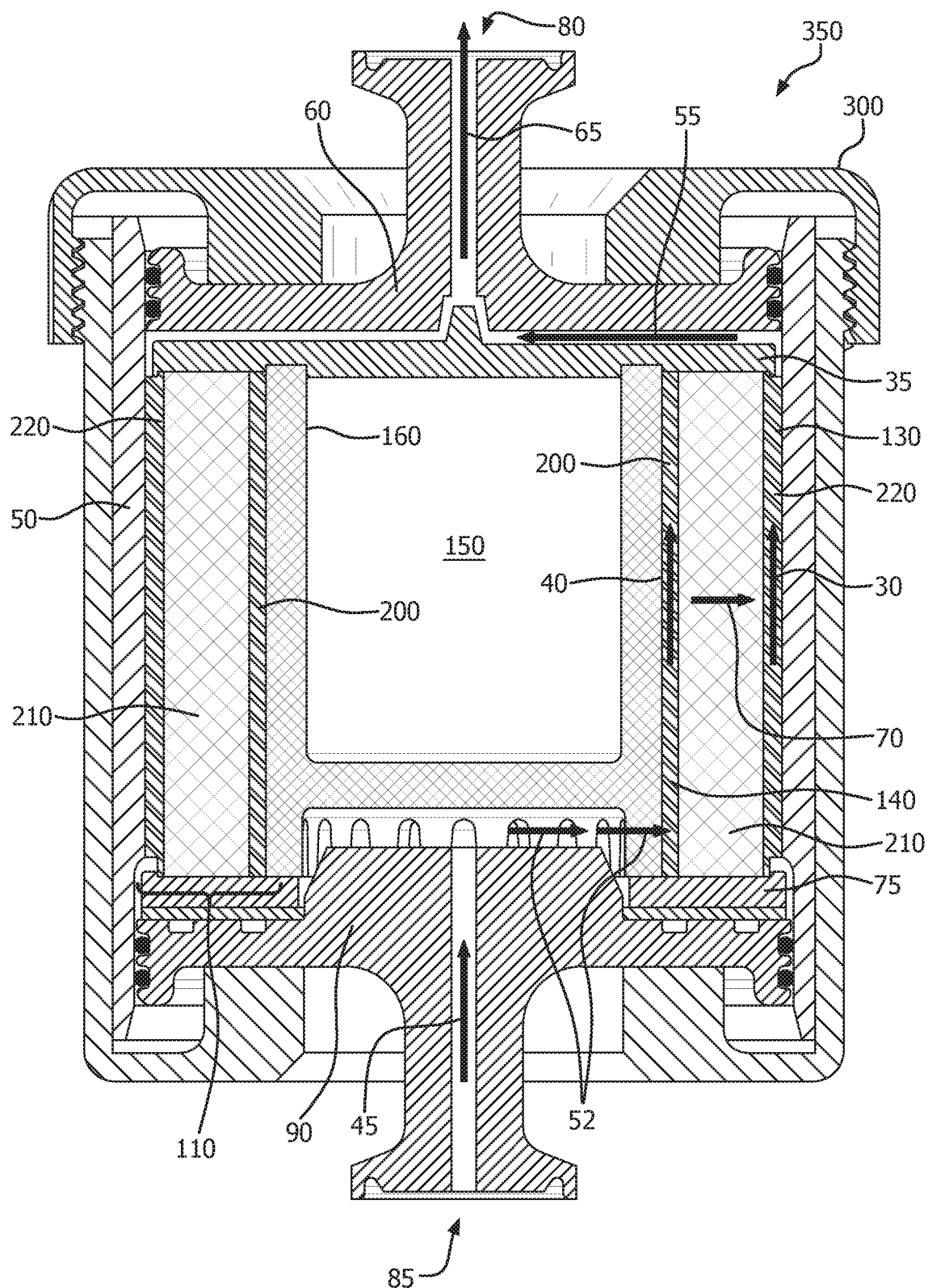
FIG. 2 is a schematic cross-section of spiral wound chromatography device that flows from an inner flow channel to an outer flow channel in accordance with at least one embodiment.

In an alternate embodiment depicted in FIG. 2, the aqueous mixture flows in the reverse direction from the chromatography device 100, i.e., through the inner flow channel 140, across the wound polymer membrane 110, and into the outer flow channel 130. In particular, the aqueous mixture flows into outlet 85 in the direction of arrow 45. The outlet flow distributor 90 and outer wall 160 direct the aqueous mixture 90 degrees from the feed direction towards the inner flow channel 140.

The aqueous mixture then flows through the inner flow channel 140 in the direction of arrow 40 and across the wound polymer membrane 210 in a normal direction (e.g., a normal flow) as shown by arrow 70. As the aqueous mixture is passed in a normal flow from the inner flow channel 140 and across the wound polymer membrane 210, the affinity ligand reversibly binds to the targeted protein. The protein-free aqueous mixture then enters the outer flow channel 130 located between the flow path housing 50 and the wound polymer membrane 210. The protein-free aqueous mixture flows through the outer flow channel 130 in direction of arrow 30.

The protein-free aqueous mixture is redirected at the end of the outer flow channel 130 by the inlet flow distributor 60 towards the central portion of the chromatography device 350, as depicted by arrow 55. The protein-free aqueous mixture then flows out of the chromatography device 350 through inlet 80 in the direction of arrow 65. As with the embodiment described above in FIG. 1, the flow path housing 50 may be positioned within a pressure containment housing 300.

The intermediate material 200, 220 is not particularly limiting so long as the aqueous mixture is able to flow therethrough. Some non-limiting examples of suitable intermediate materials include, but are not limited to, a porous fluoropolymer film or a porous non-fluoropolymer film (e.g., a porous polypropylene or other porous polyolefin film), a porous non-woven material, or a porous woven material. It is to be noted that the "spiral wound membrane assembly" and "membrane assembly" as used herein are meant to describe the polymer membrane wrapped about a core, a polymer membrane and an intermediate non-woven material wrapped about a core, as well as any combination of polymers and/or polymer and intermediate material wrapped around a core. In some embodiments, the spiral wound membrane assembly incudes an integrated inlet end cap at one end of the core and an integrated outlet end cap at an opposing end of the core to form an integrated, reusable cartridge.

Figure 3:
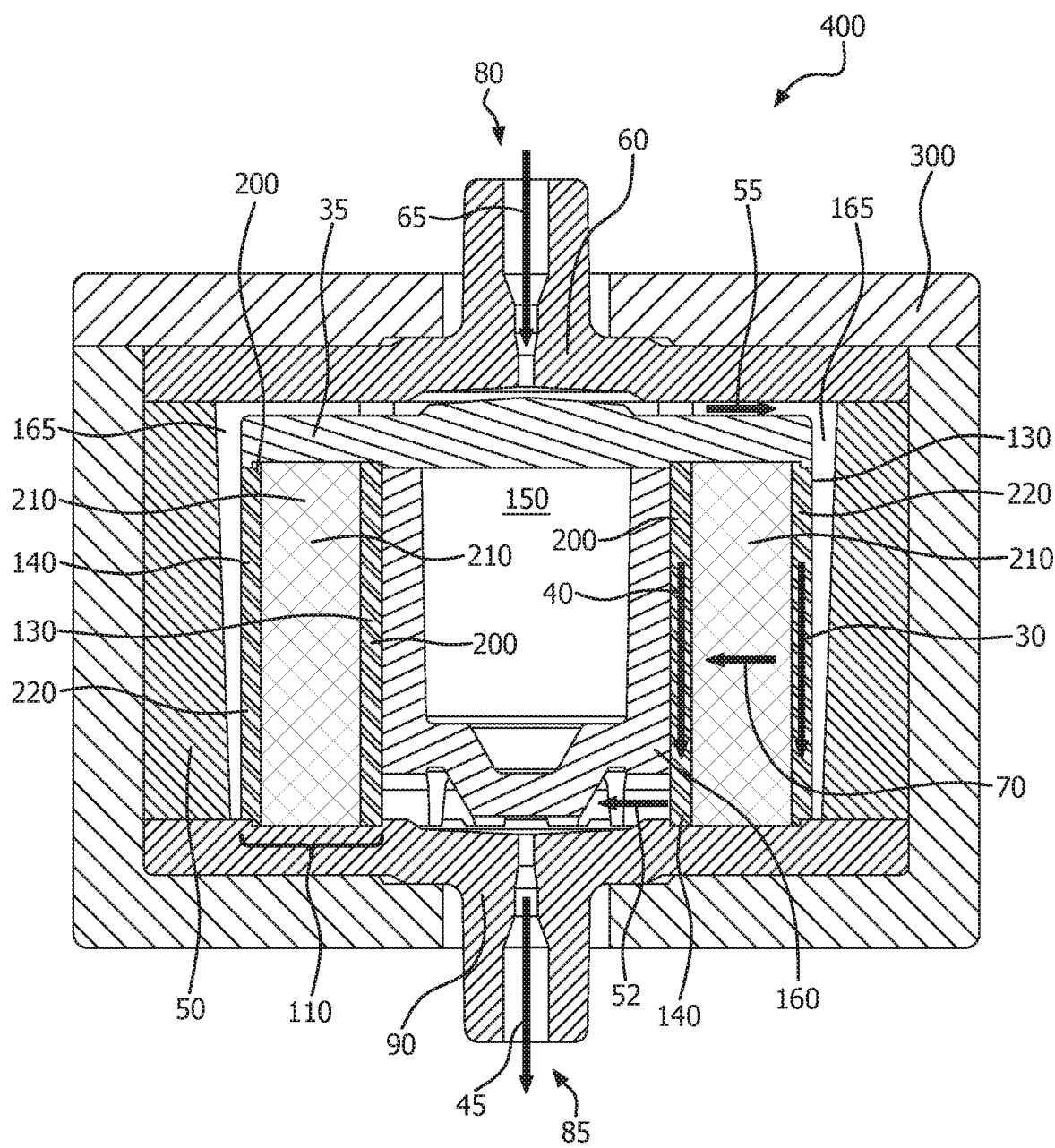
FIG. 3 is a schematic cross-section of another spiral wound, normal flow chromatography device in accordance with at least one embodiment.

In other embodiments, such as depicted in FIG. 3, there is no integrated cartridge separate from the outlet flow distributor as the outlet end cap 75 and the outlet flow distributor 90 are combined into a single piece. Instead of embedding the polymer membrane 210 into an outlet endcap 75 and then placing it next to an outlet flow distributor 90 as depicted in the embodiment shown in FIG. 1, the outlet flow distributor 90 is embedded directly to the polymer membrane 210. Thus, the outlet end cap 75 is omitted in the embodiment depicted in FIG. 3.

The function of the chromatography device 400 depicted in FIG. 3 is substantially similar to the chromatography device 100 depicted in FIG. 1. For instance, an aqueous mixture is introduced into the chromatography device 400 via an inlet 80 located within the inlet flow distributor 60 in the direction of arrow 65. The inlet flow distributor 60 and/or the inlet endcap 35 directs the aqueous mixture 90 degrees from the feed direction towards the outer flow channel 140 formed of at least one outer intermediate material. The aqueous mixture flows along the outer channel gap 165 and connects with the outer flow channel 140 (i.e., outer intermediate membrane(s)) where it flows in the direction of arrow 30. The aqueous mixture flows across the wound polymer membrane 210 in a normal direction (e.g., a normal flow) as shown by arrow 70 from the outer flow channel 140 to the inner flow channel 130. As the aqueous mixture passes through the wound polymer membrane 210, the affinity ligand reversibly binds to the targeted protein.

The protein-free aqueous mixture then is redirected at the bottom of the inner flow channel 130 by the outlet flow distributor 90 towards the central portion of the chromatography device 400 as depicted by arrow 52. The protein-free aqueous mixture flows out of the chromatography device 400 through outlet 85 positioned within the outlet flow distributor 90 in the direction of arrow 45. As with the other embodiments described herein, the flow path housing 50 may be positioned within a pressure containment housing 300.

The polymer membrane(s) contain(s) inorganic particles. In some embodiments, the polymer membrane may contain more than one type of inorganic particle and/or more than one nominal particle size within the polymer membrane. The polymer membranes may contain from about 20 mass % to about 95 mass %, from about 35 mass % to about 90 mass %, from about 50 mass % to about 90 mass %, from about 60 mass % to about 90 mass %, from about 70 mass % to about 90 mass %, or from about 80 mass % to 90 mass % inorganic particles. Non-limiting examples of suitable inorganic particles include silica, zeolites, hydroxyapatite, metal oxides, and combinations thereof. It is to be understood that the term "silica" as used herein is meant to describe a silicon dioxide that does not contain any measurable amount of boron or contains no boron as measured by x-ray photoelectron spectroscopy (XPS). Additionally, the inorganic particles may be either solid or porous and may have a variety of sizes and shapes.

The inorganic particles may have a nominal particle size of about 0.1 microns, about 0.5 microns, about 1 micron, about 5 microns, about 10 microns, about 15 microns, about 20 microns, or about 25 microns or more. Further, the inorganic particles may be monodisperse or polydisperse.

In some embodiments, the affinity ligand is covalently bonded to the inorganic particles. In another embodiments, the affinity ligand is covalently bonded to the polymer membrane. In a further embodiment, the affinity ligand may be bound to both the polymer membrane and the inorganic particle(s). The affinity ligand may be a protein, antibody, or polysaccharide that reversibly binds to a targeted protein or antibody. In one embodiment, the affinity ligand is a protein that reversibly binds, for example, to an Fc region of an antibody, an antibody fragment, an Fc fusion protein, or an antibody/drug conjugate. In another embodiment, the affinity ligand is an antibody, Protein L, or a polysaccharide that reversibly binds to a protein or a protein fragment to which it is specific. Exemplary affinity ligands for use in the affinity chromatography device include, but are not limited to, Protein A, Protein G, Protein L, human Fc receptor protein, antibodies that specifically bind to other proteins, and heparin. The affinity ligand may be native, recombinant, or synthetic. In yet another embodiment, the affinity ligand is a metal affinity ligand that reversibly binds to His-Tagged Proteins.

In at least one embodiment, the fluoropolymer membrane is a polytetrafluoroethylene (PTFE) membrane or an expanded polytetrafluoroethylene (ePTFE) membrane. Expanded polytetrafluoroethylene (ePTFE) membranes prepared in accordance with the methods described in U.S. Pat. No. 7,306,729 to Bacino et al., U.S. Pat. No. 3,953,566 to Gore, U.S. Pat. No. 5,476,589 to Bacino, or U.S. Pat. No. 5,183,545 to Branca et al. may be used herein. Further, the fluoropolymer membrane may be rendered hydrophilic (e.g., water-wettable) using known methods in the art, such as, but not limited to, the method disclosed in U.S. Pat. No. 4,113,912 to Okita, et al. A coating that effectively binds to a ligand, such as described in U.S. Pat. No. 5,897,955 to Drumheller, U.S. Pat. No. 5,914,182 to Drumheller, or U.S. Pat. No. 8,591,932 to Drumheller may be applied to the polymer membrane.

The fluoropolymer membrane may also include a polymer material comprising a functional tetrafluoroethylene (TFE) copolymer material where the functional TFE copolymer material includes a functional copolymer of TFE and PSVE (perfluorosulfonyl vinyl ether), or TFE with another suitable functional monomer, such as, but not limited to, vinylidene fluoride (VDF), vinyl acetate, or vinyl alcohol. A functional TFE copolymer material may be prepared, for example, according to the methods described in U.S. Pat. No. 9,139,707 to Xu et al. or U.S. Pat. No. 8,658,707 to Xu et al.

It is to be understood that throughout the application, the term "PTFE" is utilized herein for convenience and is meant to include not only polytetrafluoroethylene, but also expanded PTFE, expanded modified PTFE, and expanded copolymers of PTFE, such as described in U.S. Pat. No. 5,708,044 to Branca, U.S. Pat. No. 6,541,589 to Baillie, U.S. Pat. No. 7,531,611 to Sabol et al., U.S. Pat. No. 8,637,144 to Ford, and U.S. Pat. No. 9,139,669 to Xu, et al.

In one or more exemplary embodiment, the polymer membrane may be formed with one or more non-fluoropolymer materials, such as, but not limited to poly (p-xylylene) (ePPX) as taught in U.S. Patent Publication No. 2016/0032069, porous ultra-high molecular weight polyethylene (eUHMWPE) as taught in U.S. Pat. No. 9,926,416 to Sbriglia, porous ethylene tetrafluoroethylene (eETFE) as taught in U.S. Pat. No. 9,932,429 to Sbriglia, porous polylactic acid (ePLLA) as taught in U.S. Pat. No. 7,932,184 to Sbriglia, et al., porous vinylidene fluoride-co-tetrafluoroethylene or trifluoroethylene [VDF-co-(TFE or TrFE)] polymers as taught in U.S. Pat. No. 9,441,088 to Sbriglia.

Also, the polymer membrane may be, for example, a polyolefin membrane (e.g. polypropylene membrane), an organic membrane (e.g., a cellulose-based membrane), a structured hydrogel membrane, or an agarose membrane.

The affinity chromatography device described herein has a dimensionless resistance parameter that is less than 0.08, less than 0.075, less than 0.07, less than 0.065, less than 0.06, less than 0.055, less than 0.05, less than 0.045, less than 0.04, less than 0.035, less than 0.03, less than 0.025, less than 0.02, less than 0.015, or less than 0.01. The dimensionless parameter may be from about 0.001 to about 0.08, from about 0.001 to about 0.07, from about 0.001 to about 0.06, from about 0.001 to about 0.05, from about 0.001 to about 0.03, from about 0.001 to about 0.02, from about 0.001 to about 0.01. The dimensionless parameter is discussed in U.S. Pat. No. 6,257,416 to Nussbaumer and is described by the following formula:

$$A = L \cdot \sqrt{\frac{8 \cdot D \cdot d}{[(R_2+k)^2 - R_2^2] \cdot \left[(R_2+k)^2 + R_2^2 - \frac{(R_2+k)^2 - R_2^2}{\ln\left(\frac{R_2+k}{R_2}\right)}\right] \cdot \ln\left(\frac{R_2}{R_1}\right)}}$$

wherein:
$R_1$=inside radius of the adsorber hollow cylinder in cm;
$R_2$=outside radius of the adsorber hollow cylinder in cm;
k=width of the outer annular plenum in cm;
L=length of the adsorber hollow cylinder in cm;
D=flux through the individual membrane in cmcP/min·bar; and
d=thickness of the individual membrane in cm.

According to Nussbaumer, the dimensionless parameter should be between 0.08 and 0.8. The chromatography devices according to this application is able to achieve dimensionless parameters less than 0.08.

Advantageously, the chromatography device may be used multiple times. Additionally, the chromatography device may be cleaned with a caustic solution (e.g. sodium hydroxide, phosphoric acid, citric acid, ethanol, and the like) after each separation process or after multiple separation processes and reused.

Although exemplary embodiments of the membrane assembly 110 are described herein, it is to be appreciated that any number of polymer membranes as well as any and all combinations of types of polymer membranes, types of inorganic particles, sizes of inorganic particles, shapes of inorganic particles, and orientations of the polymer membranes within the membrane assembly are within the scope of this disclosure. Also, some or all of the polymer membranes may vary in composition, thickness, permeability, etc. from each other.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

EXAMPLES

Example 1

A porous PTFE membrane having 15 mass percent PTFE and 85 mass percent porous silica particles (Grace, Baltimore, MD) having a nominal particle size of 20 micron was obtained. A polypropylene non-woven material was obtained (part number T3161L from Berry Plastic, Old Hickory, TN). The polypropylene non-woven material and porous PTFE membrane were slit to a desired width using a transfer slitter with a blade box for the polypropylene non-woven material and shear cut slitters for the porous PTFE membrane. 100 cm of the polypropylene non-woven material for the inner flow channel and 120 cm of the propylene non-woven material for the outer flow channel were cut from a roll with the proper slit width using a tape measure. 248 cm of the porous PTFE membrane was cut from a roll with the proper slit width using a tape measure. The outer flow channel non-woven material was adhered to a 3 inch (approximately 7.6 cm) polyvinylchloride (PVC) core and wound around the core. The end of the polypropylene non-woven material forming the outer flow channel was bonded to one end of the porous PTFE membrane using an impulse sealer (Model KF-200H from Uline). The porous PTFE membrane was then wound on top of the polypropylene non-woven material on the core. The exposed end of the porous PTFE membrane was bonded to one end of the polypropylene non-woven material forming the inner flow channel using an impulse sealer (Model KF-200H from Uline). The inner flow channel of polypropylene non-woven material was wound on top of the porous PTFE membrane on the core. This created a batched component.

A winder with a driven take up and a mag-brake pay off was used to transfer the material of the batched component to a polypropylene core having a length of 2.9 cm and a diameter of 4.4 cm. The polypropylene core was chucked up in the take up position. The batched component was put on the payoff. The free end of the inner flow channel of polypropylene non-woven material was bonded to the polypropylene core using a soldering iron (Weller part number WSD81). A winder was then used to transfer the material from the batched component to the polypropylene core. At the end of the winding process the end of the outer flow channel polypropylene non-woven material was bonded to itself using a soldering iron (Weller part number WSD81) to prevent the windings from coming undone. This created a spiral wound membrane assembly.

The spiral wound membrane assembly was sealed using an IR servo driven plastic welder (HHPW1432S-IR TRIPLE AXIS SERVO IR Welder from Dukane). The spiral would membrane assembly and a polypropylene outlet end cap having a diameter of 7.1 cm were placed in tooling in the plastic welder. The welder heated the outlet end cap and core of the spiral would membrane assembly. The welder brought the outlet end cap and core into a bonding position to create a seal between the outlet end cap and the polypropylene core and embed the polypropylene non-woven material and porous PTFE membrane into the outlet end cap. The spiral would membrane assembly with the outlet end cap and inlet end cap were placed in the tooling in the plastic welder. The welder heated the inlet end cap (having a diameter of 6.9 cm) and the core of the spiral would membrane assembly. The welder brought the inlet end cap and polypropylene core into a bonding position to form a seal between the inlet end cap and the polypropylene core and embed the polypropylene non-woven material and porous PTFE membrane into the inlet end cap. This created an integral cartridge.

The integral cartridge was placed in an Ultem flow path housing using a gasket-ring to seal at the outlet flow distributor and silicone O-rings to seal the flow distributors to the housing. The flow path housing was then placed in an aluminum pressure containment housing. The cap on the pressure containment housing was tightened to provide sealing force to the flow path housing, thereby creating a chromatography device.

The chromatography device was washed using 95/5 ethanol/water solution and then washed a second time with DI water. An affinity ligand for reversibly binding a targeted protein or antibody was attached to the porous silica particles using a reductive amination process as is well known in the art.

The dimensionless parameter was calculated to be 0.003. The component dimensions of the wound membrane assembly are shown in Table 1. The results for the dimensionless parameter are shown in Table 2.

Example 2

The process for forming a chromatography device was conducted in the manner described in Example 1 with the exception that the polypropylene cores had a height of 5.6 cm. The dimensionless parameter was calculated to be 0.005. The component dimensions of the wound membrane assembly are shown in Table 1. The results for the dimensionless parameter are shown in Table 2.

Example 3

A porous PTFE membrane having 15 mass percent PTFE and 85 mass percent porous silica particles (Grace, Baltimore, MD) having a nominal particle size of 20 micron is obtained. A polypropylene non-woven material is obtained (part number T3161L from Berry Plastic, Old Hickory, TN). The polypropylene non-woven material and porous PTFE membrane are slit to a desired width using a transfer slitter with a blade box for the polypropylene non-woven material and shear cut slitters for the porous PTFE membrane. 100 cm of the polypropylene non-woven material for the inner flow channel and 150 cm of the propylene non-woven material for the outer flow channel are cut from a roll with the proper slit width using a tape measure. 1,130 cm of the porous PTFE membrane is cut from a roll with the proper slit width using a tape measure. The outer flow channel non-woven material is adhered to a 3 inch (approximately 7.6 cm) polyvinylchloride (PVC) core and is wound around the core. The end of the polypropylene non-woven material forming the outer flow channel is bonded to one end of the porous PTFE membrane using an impulse sealer (Model KF-200H from Uline). The porous PTFE membrane is then wound on top of the polypropylene non-woven material on the core. The exposed end of the porous PTFE membrane is bonded to one end of the polypropylene non-woven material forming the inner flow channel using an impulse sealer (Model KF-200H from Uline). The inner flow channel of polypropylene non-woven material is wound on top of the porous PTFE membrane on the core. This creates a batched component.

A winder with a driven take up and a mag-brake pay off is used to transfer the material of the batched component to a polypropylene core having a length of 5.6 cm and a diameter of 4.4 cm. The polypropylene core is chucked up in the take up position. The batched component is put on the payoff. The end of the inner channel of polypropylene non-woven material is bonded to the polypropylene core using a soldering iron (Weller part number WSD81). A winder is then used to transfer the material from the batched component to the polypropylene core. At the end of the winding process the end of the outer flow channel polypropylene non-woven material is bonded to itself using a soldering iron (Weller part number WSD81) to prevent the windings from coming undone. This creates a spiral wound membrane assembly.

The spiral wound membrane assembly is sealed using an IR servo driven plastic welder (HHPW1432S-IR TRIPLE AXIS SERVO IR Welder from Dukane). The spiral would membrane assembly and a polypropylene outlet end cap having a diameter of 11.2 cm are placed in tooling in the plastic welder. The welder heats the outlet end cap and core of the spiral would membrane assembly. The welder brings the outlet end cap and core into a bonding position to create a seal between the outlet end cap and the polypropylene core and embed the polypropylene non-woven material and porous PTFE membrane into the outlet end cap. The spiral would membrane assembly with the outlet end cap and inlet end cap are placed in the tooling in the plastic welder. The welder heats the inlet end cap (having a diameter of 11.0 cm) and the core of the spiral would membrane assembly. The welder brings the inlet end cap and polypropylene core into a bonding position to form a seal between the inlet end cap and the polypropylene core and embeds the polypropylene non-woven material and porous PTFE membrane into the inlet end cap. This creates an integral cartridge.

The integral cartridge is placed in an Ultem flow path housing using an ePTFE gasket to seal at the outlet flow distributor and silicone O-rings to seal the flow distributors to the housing. The flow path housing is then placed in an aluminum pressure containment housing. The cap on the pressure containment housing is tightened to provide sealing force to the flow path housing to create a chromatography device.

The chromatography device is washed using 95/5 ethanol/water solution and then is washed a second time with DI water. An affinity ligand for reversibly binding a targeted protein or antibody is attached to the porous silica particles using a reductive amination process as is well known in the art.

The dimensionless parameter using the above parameters for the chromatography device is calculated to be 0.005. The component dimensions of the wound membrane assembly are shown in Table 1. The results for the dimensionless parameter are shown in Table 2.

Example 4

A porous PTFE membrane having 15 mass percent PTFE and 85 mass percent porous silica particles (Grace, Baltimore, MD) having a nominal particle size of 20 micron is obtained. A polypropylene non-woven material is obtained (part number T3161L from Berry Plastics, Old Hickory, TN). The polypropylene non-woven material and porous PTFE membrane are slit to a desired width using a transfer slitter with a blade box for the polypropylene non-woven material and shear cut slitters for the porous PTFE membrane. 45 cm of the polypropylene non-woven material for the inner flow channel and 45 cm of the propylene non-woven material for the outer flow channel are cut from a roll with the proper slit width using a tape measure. 100 cm of the porous PTFE membrane is cut from a roll with the proper slit width using a tape measure. The outer flow channel non-woven material is adhered to a 3 inch (approximately 7.6 cm) polyvinylchloride (PVC) core and is wound around the core. The end of the polypropylene non-woven material forming the outer flow channel is bonded to one end of the porous PTFE membrane using an impulse sealer (Model KF-200H from Uline). The porous PTFE membrane is then wound on top of the polypropylene non-woven material on the core. The exposed end of the porous PTFE membrane is bonded to one end of the polypropylene non-woven material forming the inner flow channel using an impulse sealer (Model KF-200H from Uline). The inner flow channel polypropylene non-woven material is wound on top of the porous PTFE membrane on the core. This creates a batched component.

A winder with a driven take up and a mag-brake pay off is used to transfer the material of the batched component to a polypropylene core having a length of 2.5 cm and a diameter of 2.0 cm. The polypropylene core is chucked up in the take up position. The batched component is put on the payoff. The end of the inner flow channel polypropylene non-woven material is bonded to the polypropylene core using a soldering iron (Weller part number WSD81). A winder is them used to transfer the material from the batched component to the polypropylene core. At the end of the winding process the end of the outer flow channel polypropylene non-woven material is bonded to itself using a soldering iron (Weller part number WSD81) to prevent the windings from coming undone. This creates a spiral wound membrane assembly.

The spiral wound membrane assembly is sealed using an IR servo driven plastic welder (HHPW1432S-IR TRIPLE AXIS SERVO IR Welder from Dukane). The spiral would membrane assembly and a polypropylene outlet end cap having a diameter of 4.1 cm are placed in the tooling in the plastic welder. The welder heats the outlet end cap and core of the spiral would membrane assembly. The welder brings the outlet end cap and core into a bonding position to create a seal between the outlet end cap and the polypropylene core and embed the polypropylene non-woven material and porous PTFE membrane into the outlet end cap. The spiral would membrane assembly with the outlet end cap and inlet end cap are placed in the tooling in the plastic welder. The welder heats the inlet end cap (having a diameter of 4.0 cm) and the core of the spiral would membrane assembly. The welder brings the inlet end cap and polypropylene core into a bonding position to form a seal between the inlet end cap and the polypropylene core and embeds the polypropylene non-woven material and porous PTFE membrane into the inlet end cap. This creates an integral cartridge.

The integral cartridge is placed in an Ultem flow path housing using an ePTFE gasket to seal at the outlet flow distributor and silicone O-rings to seal the flow distributors to the housing. The flow path housing is then placed in an aluminum pressure containment housing. The cap on the pressure containment housing is tightened to provide sealing force to the flow path housing to create a chromatography device.

The chromatography device is washed using 95/5 ethanol/water solution and then is washed a second time with DI water. An affinity ligand for reversibly binding a targeted protein or antibody is attached to the porous silica particles using a reductive amination process as is well known in the art.

The dimensionless parameter using the above parameters for the chromatography device is calculated to be 0.002. The component dimensions of the wound membrane assembly are shown in Table 1. The results for the dimensionless parameter are shown in Table 2.

Example 5

A porous PTFE membrane having 15 mass percent PTFE and 85 mass percent porous silica particles (Grace, Baltimore, MD) having a nominal particle size of 20 micron is obtained. A polypropylene non-woven material is obtained (part number T3161L from Berry Plastic, Old Hickory, TN). The polypropylene non-woven material and porous PTFE membrane are slit to a desired width using a transfer slitter with a blade box for the polypropylene non-woven material and shear cut slitters for the porous PTFE membrane. 680 cm of the polypropylene non-woven material for the inner flow channel and 370 cm of the propylene non-woven material for the outer flow channel are cut from a roll with the proper slit width using a tape measure. 9,000 cm of the porous PTFE membrane is cut from a roll with the proper slit width using a tape measure. The outer flow channel non-woven material is adhered to a 3 inch (approximately 7.6 cm) polyvinylchloride (PVC) core and is wound around the core. The end of the polypropylene non-woven material forming the outer flow channel is bonded to one end of the porous PTFE membrane using an impulse sealer (Model KF-200H from Uline). The porous PTFE membrane is then wound on top of the polypropylene non-woven material on the core. The exposed end of the porous PTFE membrane is bonded to one end of the polypropylene non-woven material forming the inner flow channel using an impulse sealer (Model KF-200H from Uline). The inner channel of polypropylene non-woven material is wound on top of the porous PTFE membrane on the core. This creates a batched component.

A winder with a driven take up and a mag-brake pay off is used to transfer the material of the batched component to a polypropylene core having a length of 30.1 cm and a diameter of 19.5 cm. The polypropylene core is chucked up in the take up position. The batched component is put on the payoff. The end of the inner flow channel polypropylene non-woven material is bonded to the polypropylene core using a soldering iron (Weller part number WSD81). A winder is then used to transfer the material from the batched component to the polypropylene core. At the end of the winding process the end of the outer flow channel polypropylene non-woven material is bonded to itself using a soldering iron (Weller part number WSD81) to prevent the windings from coming undone. This creates a spiral wound membrane assembly.

The spiral wound membrane assembly is sealed using an IR servo driven plastic welder (HHPW1432S-IR TRIPLE AXIS SERVO IR Welder from Dukane). The spiral would membrane assembly and a polypropylene outlet end cap having a diameter of 34.3 cm are placed in the tooling in the plastic welder. The welder heats the outlet end cap and core of the spiral would membrane assembly. The welder brings the outlet end cap and core into a bonding position to create a seal between the outlet end cap and the polypropylene core and embed the polypropylene non-woven material and porous PTFE membrane into the outlet end cap. The spiral would membrane assembly with the outlet end cap and inlet end cap are placed in the tooling in the plastic welder. The welder heats the inlet end cap (having a diameter of 34.2 cm) and the core of the spiral would membrane assembly. The welder brings the inlet end cap and polypropylene core into a bonding position to form a seal between the inlet end cap and the polypropylene core and embeds the polypropylene non-woven material and porous PTFE membrane into the inlet end cap. This creates an integral cartridge.

The integral cartridge is placed in an Ultem flow path housing using an ePTFE gasket to seal at the outlet flow distributor and silicone O-rings to seal the flow distributors to the housing. The flow path housing is then placed in an aluminum pressure containment housing. The cap on the pressure containment housing is tightened to provide sealing force to the flow path housing to create a chromatography device.

The chromatography device is washed using 95/5 ethanol/water solution and then is washed a second time with DI water. An affinity ligand for reversibly binding a targeted protein or antibody is attached to the porous silica particles using a reductive amination process as is well known in the art.

The dimensionless parameter using the above parameters for the chromatography device is calculated to be 0.077. The component dimensions of the wound membrane assembly are shown in Table 1. The results for the dimensionless parameter are shown in Table 2.

Example 6

A porous PTFE membrane having 15 mass percent PTFE and 85 mass percent porous silica particles (Grace, Baltimore, MD) having a nominal particle size of 20 micron is obtained. A polypropylene non-woven material is obtained (part number T3161L from Berry Plastic, Old Hickory, TN). The polypropylene non-woven material and porous PTFE membrane are slit to a desired width using a transfer slitter with a blade box for the polypropylene non-woven material and shear cut slitters for the porous PTFE membrane. 110 cm of the polypropylene non-woven material for the inner flow channel and 90 cm of the propylene non-woven material for the outer feed channel are cut from a roll with the proper slit width using a tape measure. 155 cm of the porous PTFE membrane is cut from a roll with the proper slit width using a tape measure. The outer flow channel non-woven material is adhered to a 3 inch (approximately 7.6 cm) polyvinylchloride (PVC) core and is wound around the core. The end of the polypropylene non-woven material forming the outer flow channel is bonded to one end of the porous PTFE membrane using an impulse sealer (Model KF-200H from Uline). The porous PTFE membrane is then wound on top of the polypropylene non-woven material on the core. The exposed end of the porous PTFE membrane is bonded to one end of the polypropylene non-woven material forming the inner flow channel using an impulse sealer (Model KF-200H from Uline). The inner flow channel of polypropylene non-woven material is wound on top of the porous PTFE membrane on the core. This creates a batched component.

A winder with a driven take up and a mag-brake pay off is used to transfer the material of the batched component to a polypropylene core having a length of 2.1 cm and a diameter of 1.5 cm. The polypropylene core is chucked up in the take up position. The batched component is put on the payoff. The end of the inner channel of polypropylene non-woven material is bonded to the polypropylene core using a soldering iron (Weller part number WSD81). A winder is then used to transfer the material from the batched component to the polypropylene core. At the end of the winding process the end of the outer flow channel polypropylene non-woven material is bonded to itself using a soldering iron (Weller part number WSD81) to prevent the windings from coming undone. This creates a spiral wound membrane assembly.

The spiral wound membrane assembly is sealed using an IR servo driven plastic welder (HHPW1432S-IR TRIPLE AXIS SERVO IR Welder from Dukane). The spiral would membrane assembly and a polypropylene outlet end cap having a diameter of 4.7 cm are placed in the tooling in the plastic welder. The welder heats the outlet end cap and core of the spiral would membrane assembly. The welder brings the outlet end cap and core into a bonding position to create a seal between the outlet end cap and the polypropylene core and embed the polypropylene non-woven material and porous PTFE membrane into the outlet end cap. The spiral would membrane assembly with the outlet end cap and inlet end cap are placed in the tooling in the plastic welder. The welder heats the inlet end cap (having a diameter of 4.5 cm) and the core of the spiral would membrane assembly. The welder brings the inlet end cap and polypropylene core into a bonding position to form a seal between the inlet end cap and the polypropylene core and embeds the polypropylene non-woven material and porous PTFE membrane into the inlet end cap. This creates an integral cartridge.

The integral cartridge is placed in an Ultem flow path housing using an ePTFE gasket to seal at the outlet flow distributor and silicone O-rings to seal the flow distributors to the housing. The flow path housing is then placed in an aluminum pressure containment housing. The cap on the pressure containment housing is tightened to provide sealing force to the flow path housing to create a chromatography device.

The chromatography device is washed using 95/5 ethanol/water solution and then is washed a second time with DI water. An affinity ligand for reversibly binding a targeted protein or antibody is attached to the porous silica particles using a reductive amination process as is well known in the art.

The dimensionless parameter using the above parameters for the chromatography device is calculated to be 0.001. The component dimensions of the wound membrane assembly are shown in Table 1. The results for the dimensionless parameter are shown in Table 2.

TABLE 1

Component Dimensions of Wound Membrane Assembly

| Example | Core Diameter (cm) | Core Length (cm) | Inlet Cap Diameter (cm) | Outlet Cap Diameter (cm) | Inner Channel Non-woven Length (cm) | Tape Length (cm) | Outer Channel Non-woven Length (cm) |
|---|---|---|---|---|---|---|---|
| 1 | 4.4 | 2.9 | 6.9 | 7.1 | 100 | 248 | 120 |
| 2 | 4.4 | 5.6 | 6.9 | 7.1 | 100 | 248 | 120 |
| 3 | 4.4 | 5.6 | 11.0 | 11.2 | 100 | 1,130 | 150 |
| 4 | 2.0 | 2.5 | 4.0 | 4.1 | 45 | 100 | 45 |
| 5 | 19.5 | 30.1 | 34.2 | 34.3 | 680 | 9,000 | 370 |
| 6 | 1.5 | 2.1 | 4.5 | 4.7 | 110 | 155 | 90 |

TABLE 2

| Example | R1 (cm) (inner radius) | R2 (cm) (outer radius) | k (cm) (outer channel width) | L (cm) (device length) | Perm (cm^2) = D.d | A |
|---|---|---|---|---|---|---|
| 1 | 2.35 | 3.29 | 0.12 | 2.84 | 2.50E−10 | 0.003 |
| 2 | 2.35 | 3.29 | 0.12 | 5.51 | 2.50E−10 | 0.005 |
| 3 | 2.35 | 5.41 | 0.12 | 5.51 | 1.00E−09 | 0.005 |
| 4 | 1.14 | 1.84 | 0.12 | 2.42 | 2.50E−10 | 0.002 |
| 5 | 10.00 | 17.00 | 0.10 | 30.00 | 1.00E−08 | 0.077 |
| 6 | 1.14 | 2.14 | 0.13 | 2.00 | 2.50E−10 | 0.001 |

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An affinity chromatography device comprising:
an exterior housing;
an inlet flow distributor having therein an inlet to permit fluid flow into said exterior housing, said inlet flow distributor being located at a first end of said exterior housing;
a centrally located core; and
a wound membrane assembly disposed within said exterior housing, said wound membrane assembly comprising:
at least one inner intermediate material,
wherein said at least one inner intermediate material includes an inner flow channel,
a polymer membrane having therein inorganic particles having a nominal particle size; and
at least one outer intermediate material,
wherein said at least one outer intermediate material includes an outer flow channel,
wherein said at least one inner intermediate material, said polymer membrane, and said at least one outer intermediate material are positioned around said centrally located core; and
a flow distributor positioned at an opposing second end of said wound membrane assembly, wherein said flow distributor has therein an outlet to permit said fluid flow out of said exterior housing,
wherein said affinity chromatography device has a dimensionless resistance parameter that is less than 0.08, and
wherein said affinity chromatography device has a normal flow from the outer flow channel to the inner flow channel.

2. The affinity chromatography device of claim 1, wherein said dimensionless resistance parameter is less than 0.07.

3. The affinity chromatography device of claim 1, wherein said dimensionless resistance parameter is less than 0.06.

4. The affinity chromatography device of claim 1, wherein said dimensionless resistance parameter ranges from 0.001 to 0.07.

5. The affinity chromatography device of claim 1, further comprising an inlet end cap integrally connected to said wound membrane.

6. The affinity chromatography device of claim 1, wherein said at least one inner intermediate material is circumferentially positioned on an outer surface of said centrally located core to form said inner flow channel,
wherein said polymer membrane is circumferentially positioned around said at least one inner intermediate material, and
wherein said at least one outer intermediate material is circumferentially positioned on said polymer membrane to form said outer flow channel.

7. The affinity chromatography device of claim 1, wherein said at least one inner intermediate material and said at least one outer intermediate material are selected from a porous fluoropolymer film, a porous non-fluoropolymer film, a porous non-woven material, a porous woven material and combinations thereof.

8. The affinity chromatography device of claim 1, wherein said at least one inner intermediate material and said at least one outer intermediate material is a polypropylene non-woven material.

9. The affinity chromatography device of claim 1, wherein said inorganic particles are selected from silica, zeolites, hydroxyapatite, metal oxides and combinations thereof.

10. The affinity chromatography device of claim 1, wherein said polymer membrane is a porous polytetrafluoroethylene membrane.

11. The affinity chromatography device of claim 1, wherein an affinity ligand is bonded to at least one of said inorganic particles and said polymer membrane, and wherein said affinity ligand is selected from Protein A, Protein G, Protein L, human Fc receptor protein, antibodies, polysaccharides and combinations thereof.

* * * * *